(12) United States Patent
Hirota et al.

(10) Patent No.: US 9,743,825 B2
(45) Date of Patent: Aug. 29, 2017

(54) IMAGE PROCESSING APPARATUS, IMAGE PROCESSING METHOD, AND COMPUTER-READABLE RECORDING DEVICE

(71) Applicant: OLYMPUS CORPORATION, Tokyo (JP)

(72) Inventors: Masashi Hirota, Hachioji (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 336 days.

(21) Appl. No.: 14/579,425

(22) Filed: Dec. 22, 2014

(65) Prior Publication Data
US 2015/0112135 A1   Apr. 23, 2015

Related U.S. Application Data

(63) Continuation of application No. PCT/JP2013/065969, filed on Jun. 10, 2013.

(30) Foreign Application Priority Data

Jun. 28, 2012   (JP) ................. 2012-145857

(51) Int. Cl.
G06K 9/32   (2006.01)
A61B 1/00   (2006.01)
(Continued)

(52) U.S. Cl.
CPC .......... *A61B 1/00009* (2013.01); *A61B 1/04* (2013.01); *A61B 5/0075* (2013.01); *G06T 7/30* (2017.01);
(Continued)

(58) Field of Classification Search
None
See application file for complete search history.

(56) References Cited

U.S. PATENT DOCUMENTS

2007/0172150 A1*  7/2007  Quan .................. G06K 9/40
                                                  382/298
2011/0237884 A1   9/2011  Saito

FOREIGN PATENT DOCUMENTS

JP   2010279454 A   12/2010
JP   2011194151 A   10/2011
JP   2012010776 A    1/2012

OTHER PUBLICATIONS

International Search Report dated Sep. 3, 2013 received in PCT/JP2013/065969.

* cited by examiner

*Primary Examiner* — Sumati Lefkowitz
*Assistant Examiner* — David Perlman
(74) *Attorney, Agent, or Firm* — Scully, Scott, Murphy & Presser, P.C.

(57) ABSTRACT

An image processing apparatus performs positioning between a plurality of spectral band images obtained by capturing images inside a lumen using a plurality of rays of light having wavelength bands different from one another. The image processing apparatus includes: a spectral band image acquisition unit configured to acquire the spectral band images; a spatial frequency component extraction unit configured to extract feature data for each spatial frequency band from each pixel in at least one spectral band image of the spectral band images; a weight calculation unit configured to calculate weights for each spatial frequency band given to the at least one spectral band image, based on the feature data for each spatial frequency band extracted from each pixel in the at least one spectral band image; and a
(Continued)

positioning unit configured to perform positioning between the spectral band images based on the weights for each spatial frequency band.

10 Claims, 7 Drawing Sheets

(51) Int. Cl.
*A61B 1/04* (2006.01)
*A61B 5/00* (2006.01)
*G06T 7/30* (2017.01)

(52) U.S. Cl.
CPC .............. *G06T 2207/10024* (2013.01); *G06T 2207/10068* (2013.01)

PIXEL VALUE

PROFILE OF PIXEL VALUES $\frac{1}{f_n}$

COORDINATE

IMAGE PROCESSING APPARATUS, IMAGE PROCESSING METHOD, AND COMPUTER-READABLE RECORDING DEVICE

CROSS-REFERENCE TO RELATED APPLICATIONS

This application is a continuation of PCT international application Ser. No. PCT/JP2013/065969 filed on Jun. 10, 2013 which designates the United States, incorporated herein by reference, and which claims the benefit of priority from Japanese Patent Application No. 2012-145857, filed on Jun. 28, 2012, incorporated herein by reference.

BACKGROUND

1. Technical Field

The disclosure relates to an image processing apparatus, an image processing method, and a computer-readable recording device, for performing positioning between a plurality of spectral band images obtained by capturing images inside a lumen by using rays of light having wavelength bands different from one another.

2. Related Art

In recent years, endoscopes have been widely used as medical observation devices that can noninvasively observe the inside of a lumen of a patient. As an imaging method used in the endoscopes, a sequential lighting and a simultaneous lighting are known depending on a difference in illumination method. The sequential lighting is a method of performing imaging by sequentially irradiating an object (inside of the lumen) with rays of light having wavelength bands different from one another to obtain a plurality of spectral band images.

In the sequential lighting, the timing of imaging of each spectral band image varies, so that a position shift (called a color shift) occurs between the spectral band images due to effects of contraction motion of the lumen or the like. The color shift could affect the observation of the inside of the lumen, so that positioning between the spectral band images may be performed.

As a technique related to the positioning between the spectral band images, Japanese Laid-open Patent Publication No. 2011-194151 discloses a technique of performing the positioning based on blood vessel information of each spectral band image. More specifically, blood vessels whose thicknesses are different from one another are emphasized by two types of spatial filters, and the emphasized blood vessels are assumed to be a blood vessel in a surface layer and a blood vessel in an intermediate layer, respectively. Then, the positioning between a short-wavelength spectral band image and an intermediate-wavelength spectral band image is performed by using position information of the surface layer blood vessel, and the positioning between the intermediate-wavelength spectral band image and a long-wavelength spectral band image is performed by using position information of the intermediate layer blood vessel.

SUMMARY

In accordance with some embodiments, an image processing apparatus, an image processing method, and a computer-readable recording device are presented.

In some embodiments, an image processing apparatus performs positioning between a plurality of spectral band images obtained by capturing images inside a lumen by using a plurality of rays of light having wavelength bands different from one another. The image processing apparatus includes: a spectral band image acquisition unit configured to acquire the plurality of spectral band images; a spatial frequency component extraction unit configured to extract feature data for each spatial frequency band from each pixel in at least one spectral band image of the plurality of spectral band images; a weight calculation unit configured to calculate weights for each spatial frequency band given to the at least one spectral band image, based on the feature data for each spatial frequency band extracted from each pixel in the at least one spectral band image; and a positioning unit configured to perform positioning between the plurality of spectral band images based on the weights for each spatial frequency band.

In some embodiments, an image processing method for performing positioning between a plurality of spectral band images obtained by capturing images inside a lumen by using a plurality of rays of light having wavelength bands different from one another, includes: a spectral band image acquisition step of acquiring the plurality of spectral band images; a spatial frequency component extraction step of extracting feature data for each spatial frequency band from each pixel in at least one spectral band image of the plurality of spectral band images; a weight calculation step of calculating weights for each spatial frequency band given to the at least one spectral band image, based on the feature data for each spatial frequency band extracted from each pixel in the at least one spectral band image; and a positioning step of performing positioning between the plurality of spectral band images based on the weights for each spatial frequency band.

In some embodiments, a computer-readable recording device has an executable program stored thereon. The program instructs a processor for performing positioning between a plurality of spectral band images obtained by capturing images inside a lumen by using a plurality of rays of light having wavelength bands different from one another, to execute: a spectral band image acquisition step of acquiring the plurality of spectral band images; a spatial frequency component extraction step of extracting feature data for each spatial frequency band from each pixel in at least one spectral band image of the plurality of spectral band images; a weight calculation step of calculating weights for each spatial frequency band given to the at least one spectral band image, based on the feature data for each spatial frequency band extracted from each pixel in the at least one spectral band image; and a positioning step of performing positioning between the plurality of spectral band images based on the weights for each spatial frequency band.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, an image processing apparatus, an image processing method, and a computer-readable recording device according to some embodiments of the present invention will be described with reference to the drawings. The present invention is not limited by the embodiments. The same reference signs are used to designate the same elements throughout the drawings.

First Embodiment

Figure 1:
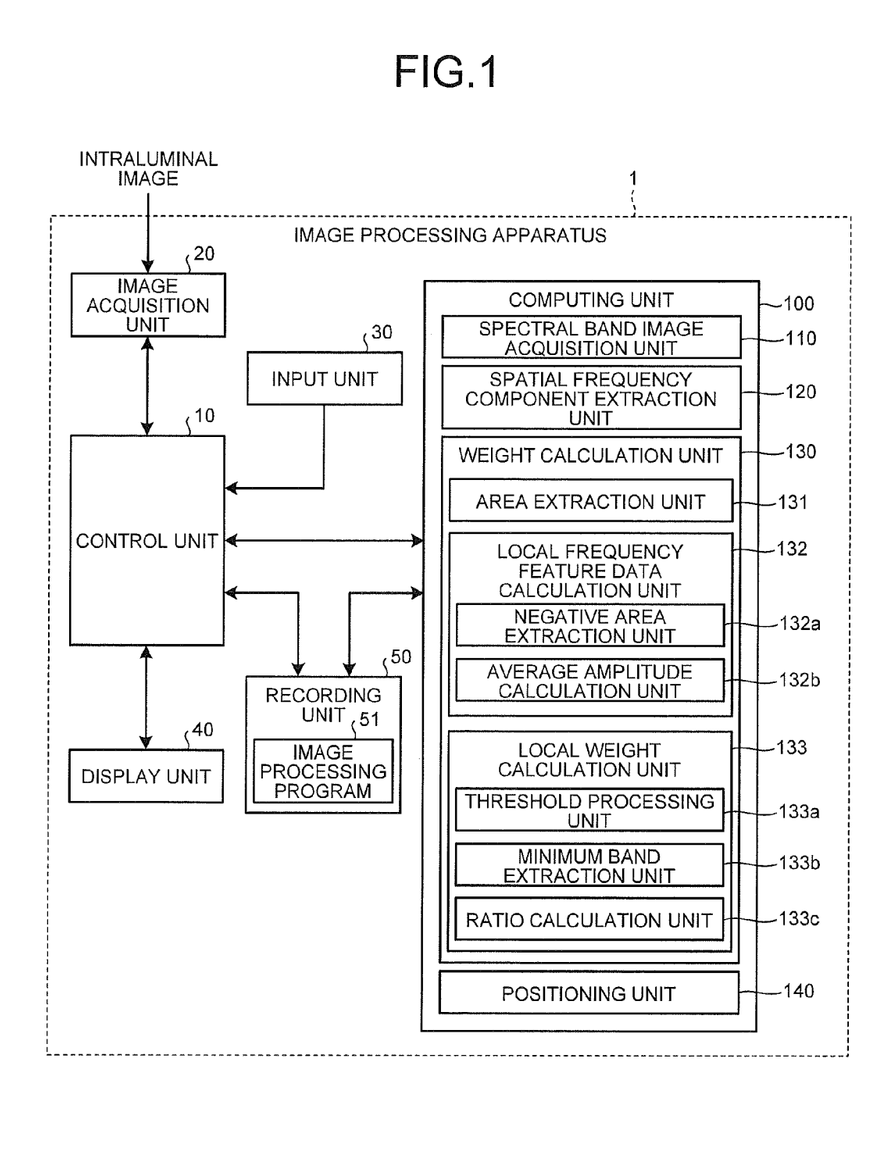
FIG. 1 is a block diagram illustrating a configuration of an image processing apparatus according to a first embodiment of the present invention.

FIG. 1 is a block diagram illustrating an image processing apparatus according to a first embodiment of the present invention. The image processing apparatus 1 according to the first embodiment is a device that performs positioning between a plurality of spectral band images acquired by capturing images inside a lumen by using a sequential lighting endoscope. In the sequential lighting, normally, spectral band images of red, green, and blue are sequentially acquired. The spectral band images are not limited to three colors of red, green, and blue, but four or more colors of spectral band images may be acquired. As an example, four colors (red (1), red (2), green, and blue) of spectral band images may be acquired by extracting two narrow bands (referred to as red (1) and red (2)) from a red band. Further, as another example, five colors (red (1), red (2), green, blue (1), and blue (2)) of spectral band images may be acquired by further extracting two narrow bands (referred to as blue (1) and blue (2)) from a blue band.

In the first embodiment, one of the sequentially acquired spectral band images of red, green, and blue is selected as a template image, and positioning is performed on each of the other spectral band images. The number of the spectral band images selected as a template image is not limited to one, but may be two or more. In this case, for example, it is possible to perform positioning of the green spectral band image by using a template created from the red spectral band image and perform positioning of the blue spectral band image by using a template created from the green spectral band image. Further, as described above, the number of the spectral band images can be four or more, so that there are various combinations of a spectral band image selected as a template and a spectral band image to be positioned.

As illustrated in FIG. 1, the image processing apparatus 1 includes a control unit 10 that controls an operation of the entire image processing apparatus 1, an image acquisition unit 20 that acquires image data corresponding to an image captured by an endoscope, an input unit 30 that receives an input signal inputted from outside, a display unit 40 that displays various things, a recording unit 50 that stores the image data acquired by the image acquisition unit 20 and various programs, and a computing unit 100 that performs specified image processing on the image data.

The control unit 10 is realized by hardware such as a CPU and transmits instructions and data to each unit included in the image processing apparatus 1 to control the operation of the entire image processing apparatus 1 according to image data inputted from the image acquisition unit 20, an operation signal inputted from the input unit 30, and the like by reading the various programs recorded in the recording unit 50.

The image acquisition unit 20 is appropriately formed according to an aspect of a system including an endoscope. For example, when a portable recording medium is used to transfer image data between the image processing apparatus 1 and a capsule endoscope, the image acquisition unit 20 includes a reader device to which the recording medium is attachably and detachably attached and which reads image data of a recorded image. When a server that stores image data of images captured by the endoscope is installed, the image acquisition unit 20 includes a communication device connected to the server and acquires the image data by communicating with the server. Alternatively, the image acquisition unit 20 may include an interface device to which an image signal is inputted from the endoscope through a cable.

The input unit 30 is realized by an input device, such as, for example, a keyboard, a mouse, a touch panel, and various switches, and outputs a received input signal to the control unit 10.

The display unit 40 is realized by a display device such as an LCD and an EL display, and displays various screens including an intraluminal image under control of the control unit 10.

The recording unit 50 is realized by various IC memories such as a RAM and a ROM including a flash memory where update recording is possible, a hard disk which is built-in or connected through a data communication terminal, an information recording device such as a CD-ROM and a reading device of the information recording device, or the like. The recording unit 50 stores a program for causing the image processing apparatus 1 to operate and causing the image processing apparatus 1 to perform various functions and data used while the program is executed in addition to the image data acquired by the image acquisition unit 20. Specifically, the recording unit 50 stores an image processing program 51 that causes the image processing apparatus 1 to perform positioning between a plurality of spectral band images acquired by the sequential lighting endoscope and various information used while the program is executed.

The computing unit 100 is realized by hardware such as a CPU. The computing unit 100 performs image processing on the intraluminal image by reading the image processing program 51 and performs positioning between a plurality of spectral band images acquired by the sequential lighting endoscope.

Next, a configuration of the computing unit 100 will be described. As illustrated in FIG. 1, the computing unit 100 includes a spectral band image acquisition unit 110 that acquires a plurality of spectral band images, a spatial frequency component extraction unit 120 that extracts feature data for each spatial frequency band from each pixel in at least one spectral band image among the plurality of spectral band images, a weight calculation unit 130 that calculates weights for each spatial frequency band given to the at least one spectral band image based on the feature data, and a positioning unit 140 that performs positioning between the plurality of spectral band images based on the weights.

The spectral band image acquisition unit 110 acquires three spectral band images of red, green, and blue, which are frame-sequentially captured, or continuous two spectral band images among the three spectral band images as spectral band images to be processed by reading image data from the recording unit 50.

The spatial frequency component extraction unit 120 determines at least one of the plurality of spectral band images as an image for creating a template used for positioning (hereinafter referred to as a template image) and extracts feature data for each spatial frequency band from each pixel in the template image.

The weight calculation unit 130 includes an area extraction unit 131 that extracts a plurality of local areas from the template image, a local frequency feature data calculation unit 132 that calculates feature data for each spatial frequency band in each local area (hereinafter referred to as a local frequency feature data) from a spatial frequency component of each pixel in the template image, and a local weight calculation unit 133 that calculates weights for each spatial frequency band given to each local area (hereinafter referred to as a local weight) based on the local frequency feature data.

Among them, the local frequency feature data calculation unit 132 includes a negative area extraction unit 132a that extracts a pixel area whose amplitude of a spatial frequency component is negative (hereinafter referred to as a negative area) from the template image and an average amplitude calculation unit 132b that calculates an average value of absolute values of amplitude in the negative area for each spatial frequency band in each local area and determines the average value calculated for each spatial frequency band as the local frequency feature data of the local area.

The local weight calculation unit 133 includes a threshold processing unit 133a that extracts spatial frequency bands whose local frequency feature data is greater than or equal to a specified threshold value, a minimum band extraction unit 133b that extracts a spatial frequency band whose local frequency feature data is the minimum from among the spatial frequency bands extracted by the threshold processing unit 133a, and a ratio calculation unit 133c that calculates a ratio of the local frequency feature data of the spatial frequency bands extracted by the threshold processing unit 133a to the local frequency feature data of the spatial frequency band extracted by the minimum band extraction unit 133b, and outputs the ratio as the local weight.

Figure 2:
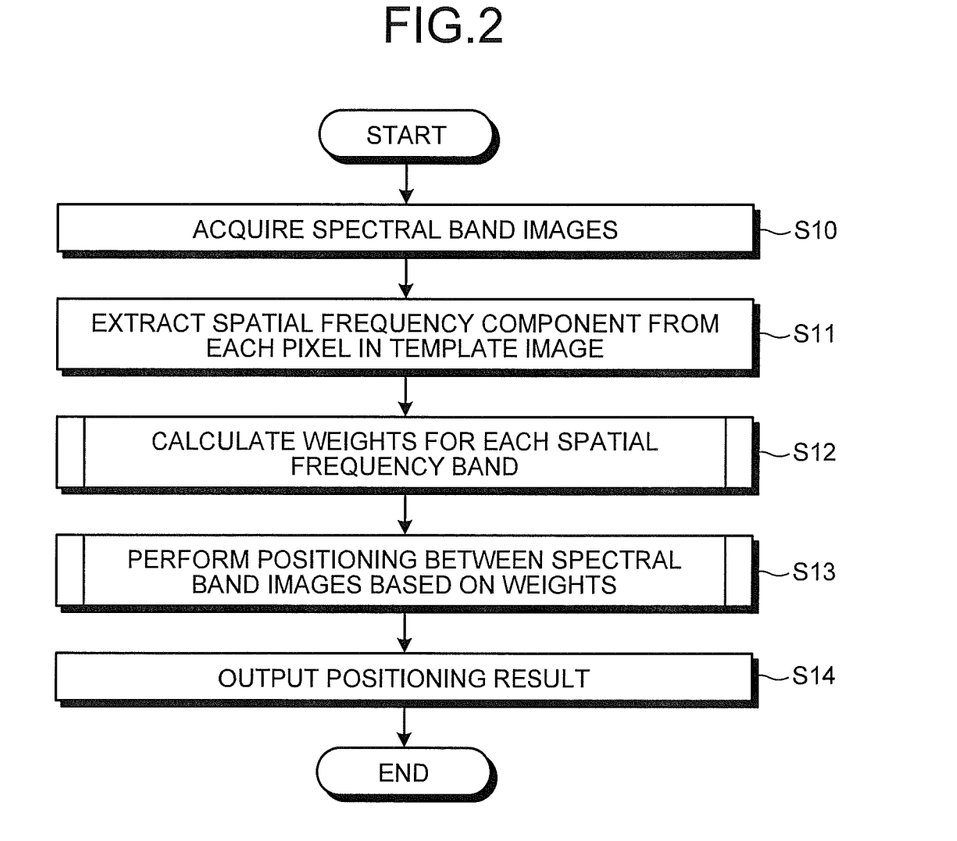
FIG. 2 is a flowchart illustrating an operation of the image processing apparatus illustrated in FIG. 1.

Next, an operation of the image processing apparatus 1 will be described. FIG. 2 is a flowchart illustrating an operation of the image processing apparatus 1.

First, in step S10, the spectral band image acquisition unit 110 reads the image data recorded in the recording unit 50 and acquires a plurality of spectral band images to be processed.

In the following step S11, the spatial frequency component extraction unit 120 selects one of the images acquired in step S10 as the template image and extracts amplitude information of a pixel value for each spatial frequency band (hereinafter referred to as a spatial frequency component) from each pixel in the template image as feature data for each spatial frequency band.

Figure 3:
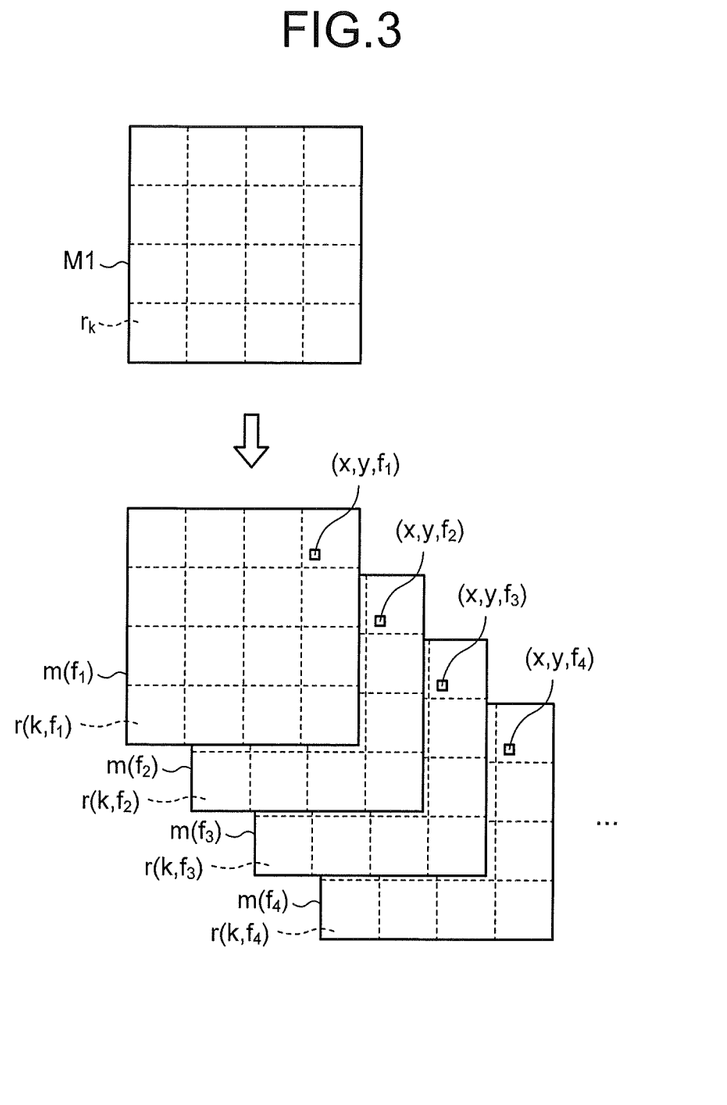
FIG. 3 is a schematic diagram illustrating images for each spatial frequency band, which are created from a template image.

In the first embodiment, the spatial frequency component of each pixel is extracted by performing DOG (Difference of Gaussian) on the template image. Here, the DOG is a process to calculate a difference between images obtained by performing Gaussian filter processes having scales different from one another on an original image (reference: Advanced Communication Media Co., Ltd. "Computer Vision and Image Media 2, p. 8") and corresponds to a bandpass filter process on an image. As illustrated in FIG. 3, each difference image $m(f_n)$ (n=1, 2, . . . ) calculated by the DOG performed on a template image M1 corresponds to an image for each spatial frequency band, and a pixel value $Y(x, y, f_n)$ of a pixel at the coordinates (x, y) in each difference image $m(f_n)$ corresponds to a spatial frequency component in a spatial frequency band $f_n$. Hereinafter, the difference image $m(f_n)$ is referred to as a band image.

In step S11, another process such as a generally known bandpass filter process may be performed if a spatial frequency component can be extracted from each pixel in the template image.

Figure 4:
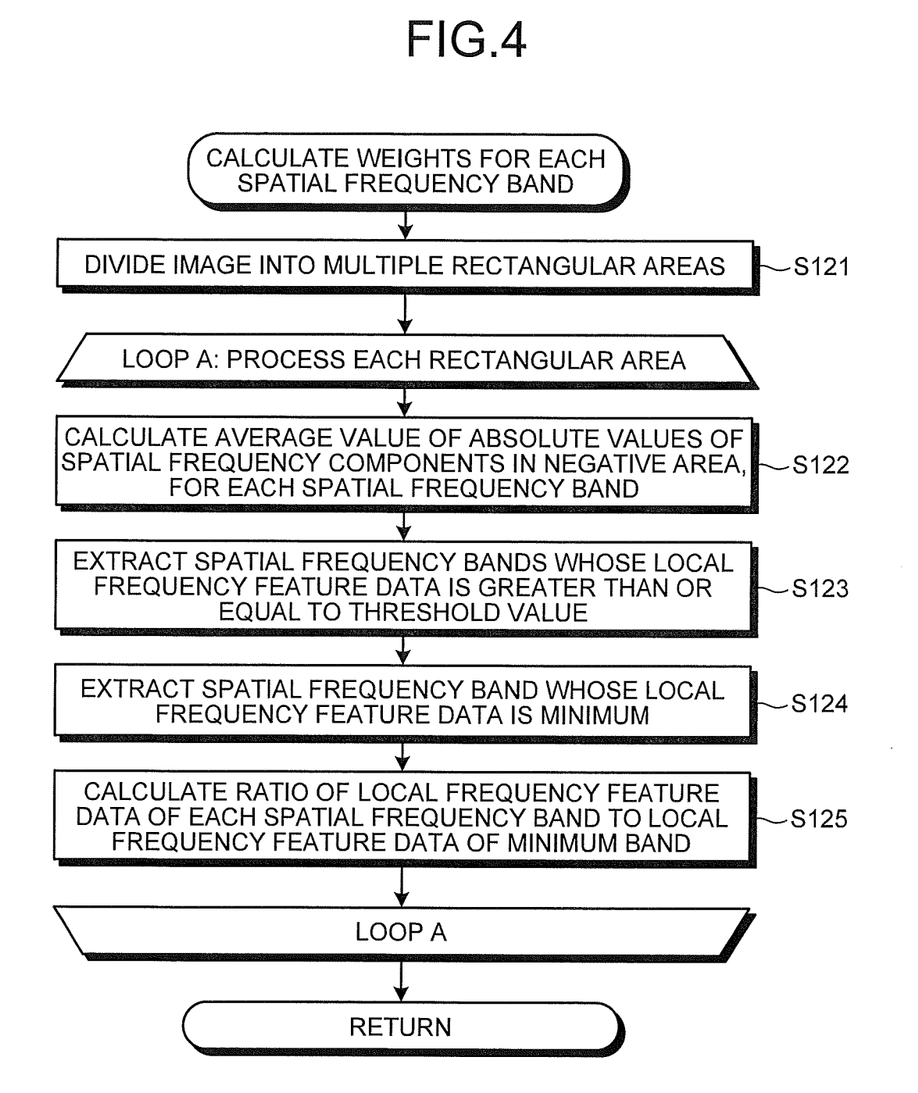
FIG. 4 is a flowchart illustrating a process performed by a weight calculation unit illustrated in FIG. 1.

In the following step S12, the weight calculation unit 130 calculates weights for each spatial frequency band based on the spatial frequency component of each pixel. FIG. 4 is a flowchart illustrating details of a process performed by the weight calculation unit 130 in step S12.

In step S121, the area extraction unit 131 divides the template image M1 into multiple rectangular areas $r_k$ as indicated by dashed lines in FIG. 3. Reference signs k (k=1, 2, . . . ) denote an alignment sequence of the rectangular areas $r_k$. The size of each rectangular area $r_k$ is determined so that the size is sufficiently greater than a wavelength corresponding to each spatial frequency band $f_n$. In FIG. 3, a rectangular area $r(k, f_n)$ indicates an area in a band image $m(f_n)$ corresponding to each rectangular area $r_k$.

Subsequently, the weight calculation unit 130 performs a process of a loop A on each rectangular area $r_k$.

Figure 5:
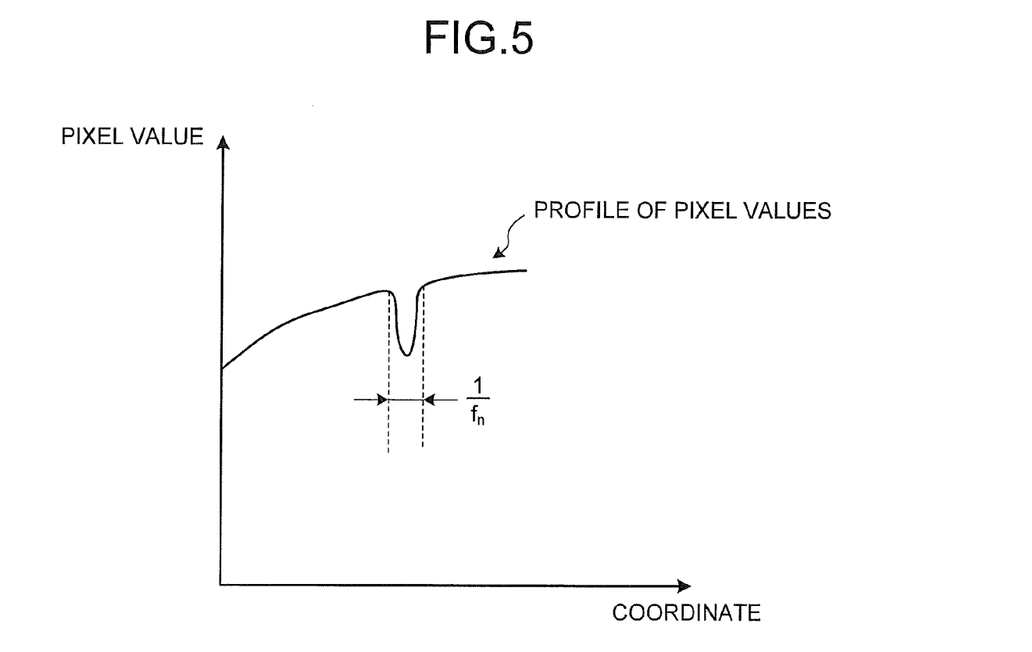
FIG. 5 is a graph illustrating an example of an area where a profile of pixel values is concave.

First, in step S122, the local frequency feature data calculation unit 132 calculates an average value of absolute values $|Y(x, y, f_n)|$ of spatial frequency components in the negative area for each spatial frequency band $f_n$. Here, the negative area in the spatial frequency band $f_n$ corresponds to an area where a profile of the pixel values is concave with a length of about $1/f_n$ with respect to surrounding areas as illustrated in FIG. 5.

More specifically, the negative area extraction unit 132a sequentially searches inside of the rectangular area $r(k, f_n)$ to be processed and extracts pixels whose spatial frequency component $Y(x, y, f_n)$ is negative. Every time a negative pixel is extracted, the average amplitude calculation unit 132b adds the spatial frequency component $Y(x, y, f_n)$ of the extracted pixel. After searching for all the pixels in the rectangular area $r(k, f_n)$, the average amplitude calculation unit 132b divides the absolute value of the sum of the spatial frequency components $Y(x, y, f_n)$ by the number of extracted pixels. Hereinafter, the average value calculated in this way is defined as local frequency feature data $c(k, f_n)$ of the spatial frequency band $f_n$ in the rectangular area $r_k$.

In step S123, the threshold processing unit 133a performs threshold processing on the local frequency feature data $c(k, f_n)$ for each spatial frequency band $f_n$ calculated in step S122 and extracts spatial frequency bands $f_n$ whose local frequency feature data $c(k, f_n)$ is greater than or equal to a specified threshold value.

In step S124, the minimum band extraction unit 133b extracts a spatial frequency band $f_{(min)}$ whose local frequency feature data $c(k, f_n)$ is the minimum (hereinafter referred to as the minimum band) from among the spatial frequency bands $f_n$ extracted in step S122.

Further, in step S125, the ratio calculation unit 133c calculates a ratio $c(k, f_n)/c(k, f_{(min)})$ of the local frequency feature data $c(k, f_n)$ of each spatial frequency band $f_n$ extracted in step S123 to the local frequency feature data $c(k, f_{(min)})$ of the minimum band $f_{(min)}$. The local weight calculation unit 133 sets the ratio $c(k, f_n)/c(k, f_{(min)})$ calculated in this way as a weight $w(k, f_n)$ for each spatial frequency band $f_n$. The weights of the spatial frequency bands $f_n$ that are not extracted in step S123 are set to 1.

By the process described above, a weight that enhances the spatial frequency bands that indicate a feature where the pixel value profile is concave as compared with the surrounding areas is set to each rectangular area $r_k$. After the process of loop A is completed for all the rectangular areas $r_k$, the process returns to a main routine.

In the first embodiment, a weight based on the local frequency feature data $c(k, f_n)$ of the minimum band $f_{(min)}$ is calculated for each of the multiple rectangular areas $r_k$ obtained by dividing the template image. However, the weight may be calculated by another method if the method can calculate a weight that enhances the spatial frequency bands $f_n$ that indicate a feature where the pixel value profile is concave as compared with the surrounding areas for each rectangular area $r_k$.

Figure 6:
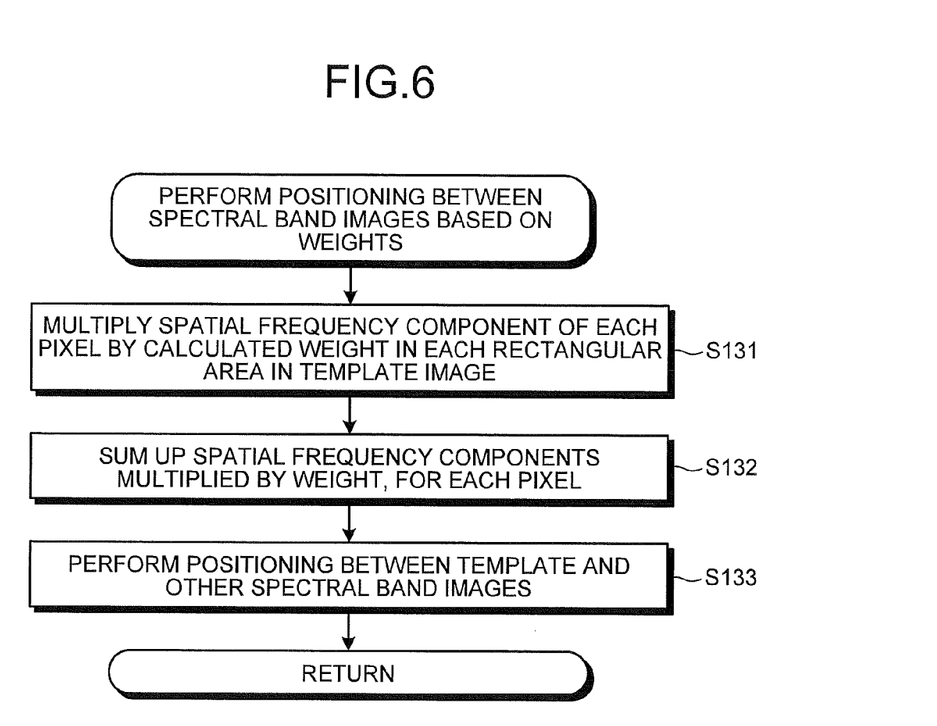
FIG. 6 is a flowchart illustrating a process performed by a positioning unit illustrated in FIG. 1.

In step S13 following step S12, the positioning unit 140 performs positioning between the spectral band images based on the calculated weights. FIG. 6 is a flowchart illustrating details of the process performed by the positioning unit 140 in step S13.

In step S131, the positioning unit 140 multiplies the spatial frequency component of each pixel by the weight $w(k, f_n)$ calculated in step S12, in each rectangular area $r_k$ in the template image M1.

In step S132, the positioning unit 140 sums up the spatial frequency components multiplied by the weight, for each pixel. Thereby, an image in which the spatial frequency components are enhanced according to the weights is created. In other words, an image in which an area where the pixel value profile is concave as compared with the surrounding areas is further enhanced is created.

In step S133, the positioning unit 140 performs positioning between the template and the other spectral band images by using the image created in step S132 as the template. As a method for the positioning, a known method such as, for example, an LK (Lucas-Kanade) method is used. Here, the LK method is a method in which when a parameter vector that represents a change of pixel coordinates between two images is $P(p_1, p_2)$, the parameter vector P where a square sum of differences of the pixel values between the two images is the minimum is obtained. By this process, pieces of coordinate information of pixels corresponding to each other are associated with each other between the spectral band image selected as the template image and the other spectral band images.

In step S14 following step S13, the computing unit 100 outputs a positioning result and stores the positioning result in the recording unit 50. At this time, the computing unit 100 may create a synthetic image in which spectral band images of red, green, and blue are superimposed based on the positioning result and display the synthetic image on the display unit 40.

As described above, in the first embodiment, a spatial frequency band including information where the pixel value profile is concave as compared with the surrounding areas is extracted and a weight that enhances amplitude information in the spatial frequency band is calculated. Specifically, frequency components that represent an area that easily absorbs irradiation light regardless of wavelength, such as a surface layer blood vessel and a minute structure of mucous membrane, are enhanced by the weights. In this way, because a template in which information that is less likely to be affected by a wavelength of a spectral band image is enhanced is created, it is possible to improve the degree of accuracy of the positioning.

In the first embodiment described above, the local frequency feature data is calculated for each of the multiple rectangular areas obtained by dividing the template image. However, the local frequency feature data may be calculated for each pixel without performing area division. In this case, it is possible to omit step S121 and step S122 illustrated in FIG. 4. Further, in step S123, for each pixel, the spatial frequency bands whose absolute value of the spatial frequency component is greater than or equal to a specified threshold value may be extracted from among the spatial frequency bands whose spatial frequency component is negative.

In the first embodiment described above, a weight of each spatial frequency band is calculated for each area obtained by dividing an image into a plurality of areas, and then the positioning is performed for each image. However, the positioning may be performed for each divided area. Here, since images to be captured in the first embodiment are images inside a lumen (images of mucous membrane), which is a non-rigid body, it can be considered that directions of position shift are different for each area. Specifically, there may be a case in which an upward position shift occurs in a certain area and a rightward position shift occurs in another area. In this case, it is possible to improve the accuracy of the positioning in the entire image by performing positioning for each area.

Alternatively, positioning may be performed for each pixel instead of performing positioning for each area. Specifically, surrounding areas are set for each pixel when the spatial frequency component is calculated and then steps S122 to S125 in FIG. 4 are performed, so that the weights of the spatial frequency components of the surrounding areas of a target pixel are calculated. Then, positioning is performed between the surrounding areas and another spectral band image by using the calculated weights. A result obtained by the above process is defined as a positioning result (deformation parameter) of each pixel.

In the first embodiment described above, one of the spectral band images of red, green, and blue is used as the template image. However, two or more spectral band images may be used as the template images. For example, it is possible to perform positioning between a template created from a red spectral band image and a green spectral band image acquired at the next timing, perform positioning between a template created from the green spectral band image and a blue spectral band image acquired at the next timing, and perform positioning between a template created from the blue spectral band image and a red spectral band image acquired at the next timing. Alternatively, as described above, by acquiring four or more spectral band images and creating templates from two or more of the spectral band images, it is possible to perform positioning by variously combine a template and a spectral band image to be positioned.

In the first embodiment described above, a process performed on a spectral band image to be positioned is not particularly mentioned. However, a specified process may be performed on the spectral band image to be positioned. For example, when, for the spectral band image to be positioned, the spatial frequencies are enhanced by using weights in the same manner as for the template and then positioning is performed by using the template, it is possible to further improve the accuracy of the positioning.

Second Embodiment

Next, a second embodiment of the present invention will be described.

Figure 7:
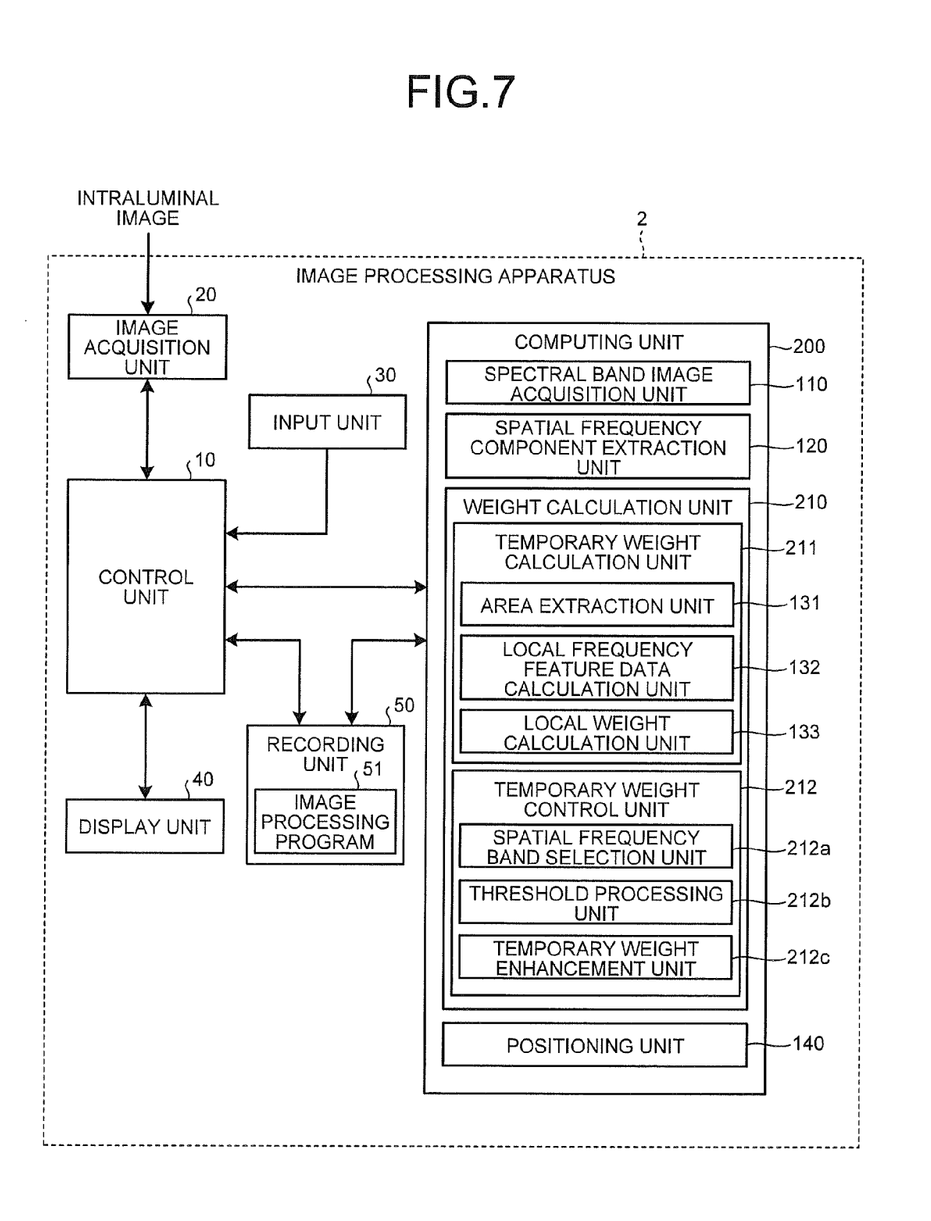
FIG. 7 is a block diagram illustrating a configuration of an image processing apparatus according to a second embodiment of the present invention.

FIG. 7 is a block diagram illustrating a configuration of an image processing apparatus according to the second embodiment of the present invention. As illustrated in FIG. 7, an image processing apparatus 2 according to the second embodiment includes a computing unit 200 including a weight calculation unit 210 instead of the weight calculation unit 130 illustrated in FIG. 1. The configuration and the operation of each unit in the computing unit 200 other than the weight calculation unit 210, and the configuration and the operation of each unit in the image processing apparatus 2 are the same as those in the first embodiment.

As illustrated in FIG. 7, the weight calculation unit 210 includes a temporary weight calculation unit 211 and a temporary weight control unit 212. The temporary weight calculation unit 211 includes the area extraction unit 131, the local frequency feature data calculation unit 132, and the local weight calculation unit 133 in the same manner as the weight calculation unit 130 in the first embodiment and outputs a weight calculated for each spatial frequency band based on the local frequency feature data as a temporary weight.

The temporary weight control unit 212 calculates a local weight by enhancing or suppressing a temporary weight in a spatial frequency band selected according to a wavelength band of the template image among the temporary weights calculated by the temporary weight calculation unit 211. More specifically, the temporary weight control unit 212 includes a spatial frequency band selection unit 212a that selects a specified spatial frequency band according to a wavelength band of the template image, a threshold processing unit 212b that performs threshold processing on local frequency feature data of the selected spatial frequency band, and a temporary weight enhancement unit 212c that enhances a temporary weight of a spatial frequency band whose local frequency feature data is determined to be greater than or equal to a specified threshold value.

Next, an operation of the image processing apparatus 2 will be described. The operation of the image processing apparatus 2 is the same as that illustrated in FIG. 2 as a whole, but a detailed process performed by the weight calculation unit 210 in step S12 is different from that in the first embodiment.

Figure 8:
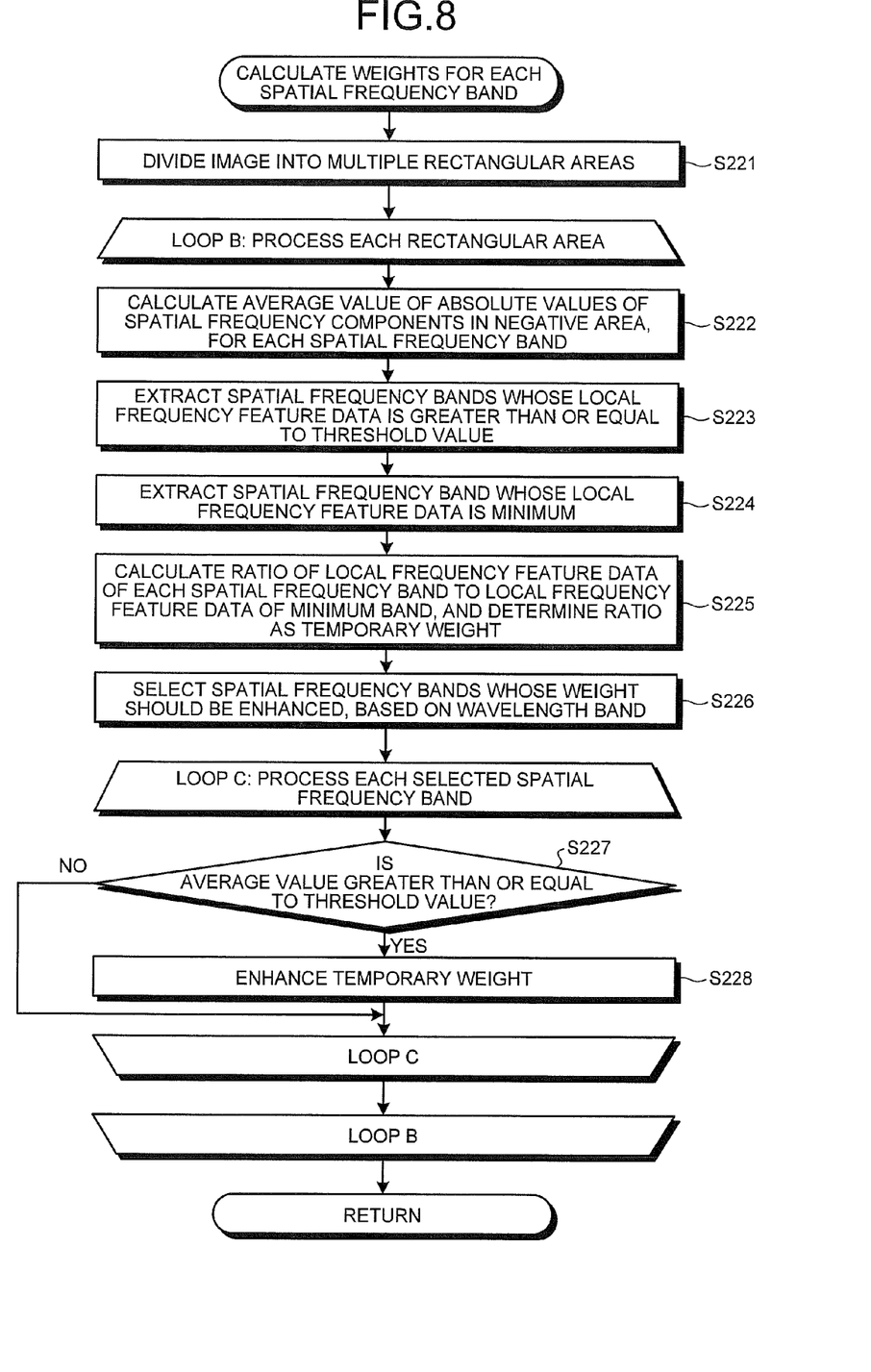
FIG. 8 is a flowchart illustrating a process performed by a weight calculation unit illustrated in FIG. 7.

FIG. 8 is a flowchart illustrating the process performed by the weight calculation unit 210 in step S12. Steps S221 to S224 illustrated in FIG. 8 correspond to steps S121 to S124 illustrated in FIG. 4.

In step S225 following step S224, the local weight calculation unit 133 calculates a ratio $c(k, f_n)/c(k, f_{(min)})$ of the local frequency feature data $c(k, f_n)$ of the spatial frequency band $f_n$ extracted in step S223 to the local frequency feature data $c(k, f_{(min)})$ of the minimum band $f_{(min)}$, and sets the ratio $c(k, f_n)/c(k, f_{(min)})$ as a temporary weight $w'(k, f_n)$ of the spatial frequency band $f_n$. The temporary weights of the spatial frequency bands $f_n$ that are not extracted in step S223 are set to 1.

In the following steps S226 to S228, the temporary weight control unit 212 controls the temporary weight according to the wavelength band of the spectral band image used as the template.

Here, information that appears as high-frequency components in the spectral band image corresponds to a minute structure of a mucous membrane surface and a minute blood vessel in a mucous membrane surface layer. Among them, the minute structure of a mucous membrane surface appears in a spectral band image regardless of the wavelength band. If a minute blood vessel also appears in a long-wavelength spectral band image (for example, a red spectral band image) where the absorbance of a blood vessel is low, there is a high probability that the same minute blood vessel appears in other spectral band images. In other words, when the intensity of high frequency components in a long-wavelength spectral band image is high, the intensity of high frequency components in other spectral band images tends to be high, so that the high frequency components are important information for the positioning. Therefore, when the template image is a long-wavelength spectral band image and the intensity of high frequency components in the spectral band image is high, the temporary weight is enhanced so that the weight of the high frequency components is large.

Therefore, in step S226, the spatial frequency band selection unit 212a selects a spatial frequency band whose weight should be enhanced based on the wavelength band of the template image. Specifically, when the template image is a red spectral band image, the spatial frequency band selection unit 212a selects a high frequency bands whose intensity (or absolute value of amplitude) of the spatial frequency component is greater than or equal to a specified threshold value and whose spatial frequency band is higher than or equal to a specified band.

Subsequently, the temporary weight control unit 212 performs a process of a loop C on each selected spatial frequency band. Specifically, in step S227, the threshold processing unit 212b determines whether or not the average value (local frequency feature data) calculated in step S222 is greater than or equal to a specified threshold value. A value greater than the threshold value in step S223 is set to the threshold value in step S227.

When the local frequency feature data is greater than or equal to the threshold value (step S227: Yes), the temporary weight enhancement unit 212c enhances the temporary weight of the spatial frequency band to be processed (see step S225) by multiplying the temporary weight by a specified coefficient (>1) (step S228). On the other hand, when the local frequency feature data is smaller than the threshold value (step S227: No), the process for the spatial frequency band ends without change.

After the process of loop C is completed for all the spatial frequency bands selected in step S226 and the process of loop B is completed for all the rectangular areas, the process returns to a main routine.

As described above, according to the second embodiment, the weight of the spatial frequency band selected according to the wavelength band of the template image is enhanced with respect to the temporary weight calculated based on the local frequency feature data. Therefore, it is possible to improve the accuracy of the positioning between the spectral band images by using the weight as described above.

First Modified Example

Next, regarding the second embodiment, a case will be described in which the template image is an extremely short wavelength spectral band image. When an extremely short wavelength spectral band image is used as the template image, if a spatial frequency component higher than a high frequency component that can be extracted from other spectral band images is extracted, such a spatial frequency component may be suppressed. This is because such a frequency component is difficult to appear in other spectral band images and is difficult to use for the positioning.

As a specific process, in step S226, when the template image is an extremely short wavelength spectral band image, the spatial frequency band selection unit 212a selects a high frequency band whose spatial frequency band is higher than or equal to a specified band. Further, in step S228, the temporary weight enhancement unit 212c multiplies a temporary weight where the local frequency feature data is determined to be greater than or equal to a specified threshold value by a specified coefficient (<1). Thereby, it is possible to suppress the temporary weight of the selected spatial frequency band.

According to the first modified example described above, because it is possible to create a template in which information that is difficult to use for the positioning is suppressed, it is possible to improve the accuracy of the positioning and reduce processing time required for the positioning.

Second Modified Example

In the first and the second embodiments described above, the weight or the temporary weight for each spatial frequency band in each rectangular area is calculated by using spatial frequency components in an image space. However, the same weight or temporary weight may be calculated by using information in a frequency space. Hereinafter, a specific process using the information in a frequency space will be described. In the description below, a case in which a weight corresponding to the first embodiment is calculated will be described. However, when a temporary weight corresponding to the second embodiment is calculated, the process is the same.

The weight calculation unit 130 divides a spectral band image into multiple rectangular areas in step S121 in FIG. 4 and then converts information in an image space into information in a frequency space by performing Fourier transform on each rectangular area. Then, the weight calculation unit 130 calculates a power (intensity) spectrum in one or more spatial frequency bands that are set in advance.

Thereafter, the weight calculation unit 130 skips step S122 and performs steps S123 to S125 by using the intensity of each spatial frequency band calculated for each rectangular area as the local frequency feature data. Specifically, the weight calculation unit 130 extracts spatial frequency bands whose intensity is greater than or equal to a specified threshold value and extracts a spatial frequency band whose intensity is the smallest (minimum band) from among the extracted spatial frequency bands. Then, the weight calculation unit 130 calculates a ratio of the intensity of each spatial frequency band to the intensity of the minimum band as a weight of each spatial frequency band.

Third Modified Example

In the first and the second embodiments described above, a template in which spatial frequency components are enhanced based on the weights calculated for each spatial frequency component for each rectangular area is created, and the positioning between the template and other spectral band images is performed by using a general positioning method (LK method or the like) using the template. However, the positioning method is not limited to the method described above. In the third modified example, another example of the positioning method will be described.

First, the positioning unit 140 divides a spectral band image to be positioned into images of each of a plurality of spatial frequency bands (hereinafter referred to as band images) by a DOG process. Then, the positioning unit 140 performs positioning between each band image and a template and calculates a deformation parameter for each spatial frequency band. Here, the deformation parameter is, for example, a parallel movement amount and an enlargement or reduction scale of objects corresponding to each other between two images. Further, the positioning unit 140 calculates an average value between all the spatial frequency bands by multiplying the weight of each spatial frequency band calculated by the weight calculation unit 130 and the deformation parameter together. The positioning unit 140 outputs the deformation parameter on which the weighted averaging processing is performed in this way as a comprehensive positioning result between the template and the spectral band image to be positioned.

The image processing apparatus according to the first and the second embodiments and the first to third modified examples of the embodiments can be realized by executing an image processing program recorded in a recording device on a computer system such as a personal computer and a workstation. Further, such a computer system may be used by connecting the computer system to another computer system or a device such as a server through a local area network (LAN), a wide area network (WAN), or a public line such as the Internet. In this case, the image processing apparatuses according to the first and the second embodiments and the first to third modified examples of the embodiments may acquire image data of an intraluminal image through these networks, output an image processing result to various output devices (viewer, printer, and the like) connected through these networks, and store an image processing result in a storage device (an information recording device and a reading device thereof, and the like) connected through these networks.

According to some embodiments, because weights for each spatial frequency band given to at least one spectral band image are calculated based on feature data for each spatial frequency band extracted from each pixel in the at least one spectral band image, it is possible to perform positioning effectively using characteristics of a spatial frequency band that is less likely to be affected by a wavelength of a spectral band image by using the weights. Therefore, it is possible to perform accurate positioning between a plurality of spectral band images.

The present invention is not limited to the first and the second embodiments and the first to third modified examples of the embodiments, but various inventions can be formed by appropriately combining a plurality of elements disclosed in the embodiments and the modified examples. For example, the invention may be made by removing some elements from all the elements described in each of the embodiments and the modified examples or may be made by appropriately combining elements described in different embodiments and modified examples.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for performing positioning between a plurality of spectral band images obtained by capturing images inside a lumen by using a plurality of rays of light having wavelength bands different from one another, the image processing apparatus comprising:
a processor comprising hardware, wherein the processor is configured to:
acquire the plurality of spectral band images;

extract feature data for each spatial frequency band from each pixel in at least one spectral band image of the plurality of spectral band images;

extract, for each spatial frequency band, a pixel area whose spatial frequency component is negative, from the at least one spectral band image, based on the feature data for each spatial frequency band extracted from each pixel in the at least one spectral band image;

calculate, for each spatial frequency band, weights for enhancing a spatial frequency component in a spatial frequency band including information in which a pixel value profile is concave as compared with surrounding areas; and perform positioning between the plurality of spectral band images based on the weights for each spatial frequency band.

2. The image processing apparatus according to claim 1, wherein the processor is configured to:

extract a plurality of local areas from the at least one spectral band image;

calculate local frequency feature data which is feature data for each spatial frequency band in each of the plurality of local areas, from the feature data for each spatial frequency band extracted from each pixel in the at least one spectral band image; and calculate weights for each spatial frequency band given to each of the plurality of local areas, as local weights, based on the local frequency feature data.

3. The image processing apparatus according to claim 2, wherein the processor is configured to calculate the local weights based on a wavelength band of the at least one spectral band image in addition to the local frequency feature data.

4. The image processing apparatus according to claim 3, wherein the processor is configured to enhance or suppress a local weight in a spatial frequency band selected according to the wavelength band from among the local weights calculated based on the local frequency feature data.

5. The image processing apparatus according to claim 4, wherein the processor is configured to:

perform threshold processing on the local frequency feature data of the spatial frequency band selected according to the wavelength band; and multiply the weight calculated based on the local frequency feature data by a specified coefficient, in the spatial frequency band where the local frequency feature data is determined to be greater than or equal to a specified threshold value by the processor.

6. The image processing apparatus according to claim 2, wherein the processor is configured to:

extract a negative area which is a pixel area where amplitude of a spatial frequency component is negative, from the at least one spectral band image;

calculate an average value of absolute values of amplitude in the negative area, for each spatial frequency band, in each of the plurality of local areas; and determine the average value calculated for each spatial frequency band as the local frequency feature data in each of the plurality of local areas.

7. The image processing apparatus according to claim 2, wherein the processor is configured to:

extract spatial frequency bands whose local frequency feature data is greater than or equal to a specified threshold value;

extract a spatial frequency band whose local frequency feature data is minimum from among the spatial frequency bands extracted by the processor; and calculate a ratio of the local frequency feature data of the spatial frequency bands extracted by the processor to the local frequency feature data of the spatial frequency band extracted by the processor.

8. The image processing apparatus according to claim 1, wherein the processor is configured to create a template by enhancing a pixel value of each pixel in the at least one spectral band image by using the weights for each spatial frequency band and to perform the positioning between the plurality of spectral band images by using the template.

9. An image processing method for performing positioning between a plurality of spectral band images obtained by capturing images inside a lumen by using a plurality of rays of light having wavelength bands different from one another, the image processing method comprising:

acquiring the plurality of spectral band images;

extracting feature data for each spatial frequency band from each pixel in at least one spectral band image of the plurality of spectral band images;

extracting, for each spatial frequency band, a pixel area whose spatial frequency component is negative, from the at least one spectral band image, based on the feature data for each spatial frequency band extracted from each pixel in the at least one spectral band image;

calculating, for each spatial frequency band, weights for enhancing a spatial frequency component in a spatial frequency band including information in which a pixel value profile is concave as compared with surrounding areas; and performing positioning between the plurality of spectral band images based on the weights for each spatial frequency band.

10. A computer-readable recording device with an executable program stored thereon, the program instructing a processor for performing positioning between a plurality of spectral band images obtained by capturing images inside a lumen by using a plurality of rays of light having wavelength bands different from one another, to execute:

acquiring the plurality of spectral band images;

extracting feature data for each spatial frequency band from each pixel in at least one spectral band image of the plurality of spectral band images;

extracting, for each spatial frequency band, a pixel area whose spatial frequency component is negative, from the at least one spectral band image, based on the feature data for each spatial frequency band extracted from each pixel in the at least one spectral band image;

calculating, for each spatial frequency band, weights for enhancing a spatial frequency component in a spatial frequency band including information in which a pixel value profile is concave as compared with surrounding areas; and performing positioning between the plurality of spectral band images based on the weights for each spatial frequency band.

* * * * *